United States Patent [19]
Beck et al.

[11] Patent Number: 4,732,763
[45] Date of Patent: Mar. 22, 1988

[54] ACTIVE/PASSIVE IMMUNIZATION OF THE INTERNAL FEMALE REPRODUCTIVE ORGANS

[75] Inventors: Lee R. Beck; Charles F. Flowers; Donald R. Cowsar; Albert C. Tanquary, all of Birmingham, Ala.

[73] Assignee: Stolle Research and Development Corporation, Cincinnati, Ohio

[21] Appl. No.: 655,989

[22] Filed: Sep. 28, 1984

Related U.S. Application Data

[63] Continuation of Ser. No. 121,480, Feb. 14, 1980, abandoned, which is a continuation-in-part of Ser. No. 952,109, Oct. 17, 1978, abandoned.

[51] Int. Cl.$^4$ .................... A61K 39/02; A61K 39/12; A61K 9/50
[52] U.S. Cl. ..................... 424/433; 424/78; 424/85; 424/86; 424/87; 424/88; 424/92; 424/89; 514/931; 514/932; 514/963
[58] Field of Search .................. 424/14–22, 424/78, 85–92, 433; 514/931, 932, 963

[56] References Cited

U.S. PATENT DOCUMENTS

| | | | |
|---|---|---|---|
| 3,490,454 | 1/1970 | Goldfarb et al. | 128/285 |
| 3,594,468 | 7/1971 | Saurino et al. | 424/25 |
| 3,691,271 | 9/1972 | Charle et al. | 424/28 |
| 3,755,558 | 8/1973 | Scribner | 424/47 |
| 3,773,919 | 11/1973 | Boswell et al. | 424/19 |
| 3,875,300 | 4/1975 | Homm et al. | 424/28 |
| 3,887,699 | 6/1975 | Yolles | 424/19 |
| 3,918,452 | 11/1975 | Cornfield | 128/270 |
| 3,921,636 | 11/1975 | Zaffaroni | 128/260 |
| 3,991,766 | 11/1976 | Schmitt et al. | 128/335.5 |
| 4,166,800 | 9/1979 | Fong | 252/316 |

OTHER PUBLICATIONS

Gardner et al., ACS Symp., Ser. 33, pp. 171-181 (1976).
Yolles et al., ASC Symp., Ser. 33, pp. 123-134 (1976).
Duncan et al., "Sustained Release Systems for Fertility Control", *Human Reproduction: Conception and Contraception*, Harper and Rowe, N.Y., 1973, pp. 500-501.
Sundaram et al., Contraception 14(6):639-654 (1976) The Effectiveness in Rhesus Monkeys of an Antifertility Vaccine Based on Neutralization of Chorionic Gonadotropin.
Moudgal et al., Fertility & Sterility 30(2):223-229 (1978) Passive Immunization with an Antibody to the B-Subunit of Ovine Luteinizing Hormone as a Method of Early Abortion–A Feasibility Study in Monkeys (MACACA RADIATA).
Thanauala et al., J. Reprod. Immunology 1:263-273 (1979) Characterization of the Immunological Response in Marmoset Monkeys Immunized Against HCG B-Subunit and its Relationship with their Subsequent Fertility.
Osra et al., J. Immunology 110(5):1307-1311, May 1973, Local Antibody Response to Poliovaccine in the Human Female Genital Tract.
Beck et al., Biology of Reproduction 13(1):10-16 (1975) Absorption of Antibodies from the Baboon Vagina (Crib Admn. of Gonadotrophnn Cross-Reacting Antibodies by Vaginal Route as Fertility Control Possibility).
Chang J. Bioengineering 1(1):25-32 (1976) Biodegradable Semipermeable Microcapsules Containing Enzymes, Hormones, Vaccines and Other Biologicals.
Jack Anicz et al., Contraception 8:227-234 (1973) Polylactic Acid as a Biodegradable Carrier for Contraceptive Steroids.
(List continued on next page.)

*Effects of Immunity Against Reproductive Hormones,* edited by Edwards and Johnson, pp. 229-242 (1976).

*Primary Examiner*—Ronald W. Griffin
*Attorney, Agent, or Firm*—Oblon, Fisher, Spivak, McClelland & Maier

[57] ABSTRACT

Antibody or antigen containing microparticles for the active or passive immunization of the internal female reproductive organs, comprising: microparticles of an antigen or antibody incorporated in a matrix material which is biocompatible and biologically degradable, said microparticles capable of being transported after deposition in the vagina by the natural transport mechanism of the internal female reproductive organs across the cervix into the uterus.

19 Claims, 5 Drawing Figures

OTHER PUBLICATIONS

Anderson et al., Contraception 13(3):375-384 (1976) An Injectable Sustained Release Fertility Control System.

Gresser et al., Contraception 17(3):253-266 (1978) Larger Animal Testing of an Injectable Sustained Release Fertility Control System.

Beck et al., Am. J. Obstetrics Gynecology 135(3):419-426 (1979) New Long-Lasting Injectable Microcapsule Contraceptive System.

Beck et al., Fertility & Sterility 31(5):545-551 (1979) A New Long-Lasting Injectable Microcapsule System for the Administration of Progesterone.

V. C. Stevens, *Antifertility Effects from Immunizations with Intact, Subunits and Fragments of HCG*, in *Physiological Effects of Immunity Against Reproductive Hormones*, edited by Edwards and Johnson, pp. 249-264 (1976).

J. P. Hearn et al., *The Effects of Immunizing Marmoset Monkeys Against the B Subunit of HCG*, in *Physiological*

ACTIVE/PASSIVE IMMUNIZATION OF THE INTERNAL FEMALE REPRODUCTIVE ORGANS

CROSS REFERENCE TO RELATED APPLICATIONS

This application is a continuation of application Ser. No. 121,480, filed Feb. 14, 1980 which in turn is a continuation-in-part of application Ser. No. 952,109, filed Oct. 17, 1978, now both abandoned.

BACKGROUND OF THE INVENTION

1. Field of the Invention

The present invention relates to a method for introducing therapeutic or medicinal agents into the uterus and fallopian tubes. More particularly, the invention relates to a method of eliciting an active or passive immunization response in the internal female reproduction organs by introducing microparticles containing a specific antibody or antigen into the vagina and allowing the microparticles to be drawn through the cervix into the uterus.

2. Description of the Prior Art

In the past, the methods of generally treating the internal reproductive organs of the female have included principally the oral ingestion or the injection of drugs into the patient in order to treat diseases and to regulatd the female reproductive cycle. No methods are known of treating the uterus and fallopian tubes by introducing a drug directly into the vagina where the natural transport mechanism of the internal reproductive organs conveys the drug across the cervix into the uterus. Yet, such a direct technique of locally introducing drugs into the vagina would be highly advantageous from the viewpoint of rapidly and effectively conveying drugs across the cervix into the uterus. This technique would be especially useful for the delivery of biologically active substances, such as antibodies and antigens, directly into the uterus to increase the level of immunization of the femal reproductive organs. Because systemic antibodies are not secreted by the internal reproductive organs, the immunization levels of these organs cannot be increased by systemic administration of either antibodies or antigens, but rather must be increased by local administration of antibodies or antigens to the female reproductive organs.

In the past various drugs and cosmetic agents have been encapsulated in the form of microcapsules for the purpose of delivering these agents to the vagina by slow, sustained release of the agent from the microcapsules. However, these techniques have only been useful in the treatment of the vagina and not the other internal female reproductive organs. For example, Zaffaroni in U.S. Pat. No. 3,921,636 shows a drug delivery device in which microcapsules containing a medicinal agent are incorporated in a carrier device such as a tampon, sanitary napkin or intrauterine device. Thus, a tampon containing microencapsulated contraceptive hormone can be inserted into the vagina and the hormone will be gradually released by dissolution of the microcapsules. Since the hormone is released in the vagina, the vagina is the site in which the hormone is absorbed by the body. This technique does not provide a means of delivering drugs to the uterus by transport across the cervix.

U.S. Pat. No. 3,918,452 shows a technique in which a contraceptive agent is delivered to the vagina by inserting a tampon containing microcapsules composed of a contraceptive composition into the vagina. The contraceptive agent such as a spermicide is then released slowly with time into the vagina where the contraceptive agent has its effect. In this technique the effects of the contraceptive agent are limited only to the vagina and not to any other portions of the internal female reproductive organs.

Because it would be highly desirable to be able to introduce medicinal agents or therapeutic agents directly into the uterus and Fallopian tubes by transport of said agents across the cervix, various techniques have been attempt to achieve this end. One approach that has been suggested is to encapsulate a medicinal or therapeutic agent in the form of microcapsules and then deposit the microcapsules in the vagina whereupon the microcapsules are transported. As a result of some early investigations, it is known that carbon particles from a cap containing a suspension of carbon particles, when placed over the cervix, can be recovered from the uterus after coitus, as shown by Amersbach, "Sterilität Und Frigidität," *München. Med. Wchnschr.* 77: 225, 1930. This shows that nonmotile particles migrate in the female reproductive tract. It was also demonstrated by J. Trapl, "Neuve Anschauunger über den Ei- und Samentransport in den Geschlechtsteilen de Frau," *Zentralbl. Gynak.* 67: 547, 1943, that even without the use of a cervical cap, carmine particles migrate thus demonstrating that nonmotile particles other than carbon also migrate.

Still other investigators, R. Krehbiel and H. P. Carstens, "Roentgen Rabbit", *Am. J. Physiol.* 125: 571, 1959, have shown that the passage of the radio-opaque oil, when placed in the vagina of a rabbit was blocked until after the vulva was stimulated. Stimulation of the vulva caused contraction waves which transported the oil into the uterus and up into the uterolubal junction within several seconds. Other earlier investigations found that graphite and dyes in gelatin were not transported whether applied to the vagina before or after copulation, but carmine particles in cocoa butter were transported to the uterus and tubes. The implication of the data is that the nature of the particles affects the transport process and that transport is assisted by muscular contractions. Hartman, in "How Do Sperms Get Into the Uterus?" *Fertil. and Steril* 8: 403, 1957, concluded that the transport of sperm in the reproductive tract, transport occurs principally by cooperation of the particles with the musculature of the female reproductive tract. He also concluded that the function of the flagellum of the sperm is to aid in the penetration of the head of the sperm into corona radiata, the zona pellucida and the vitelline membrane of the ovum. G. M. Duncan and D. R. Kalkwarf, "Sustained Release Systems for Fertility Control," in *Human Reproduction: Conception and Contraception*, edited by E. S. E. Hafez and T. N. Evans, Harper and Row, New York, 1973, have concluded from experiments that non-motile particles which are about the size of the head of the sperm migrate directionally through the cervix to the fallopian tubes. Thus, the reference indicates that non-motile particles of a size of 5 μm or less migrate throughout the internal reproductive organs when introduced into the vagina. However, when microcapsules of progesterone encapsulated within a suitable wall material such as cellulose acetate butyrate and of a size ranging from 5 to 1400 μm were introduced into the vagina, the microcapsules did not migrate across the cervix into the uterus, but rather were transported in the reverse direction. Therefore, the reference clearly suggests that microcapsules of a size greater than 5 μm will not migrate inward to the internal female reproductive organs.

A need therefore, continues to exist for a method by which various disorders and diseases of the internal female reproductive organs can be locally treated by applying microparticles of various medicinal and therapeutic agents to the vagina and allowing the natural transport mechanism of the organs to draw the microparticles across the cervix into the uterus where the medicinal or therapeutic agent is delivered to the uterus and other internal organs.

SUMMARY OF THE INVENTION

Accordingly, one object of the present invention is to provide a method by which medicinal and therapeutic agents can be locally administered to the vagina and transported through the cervix into the uterus to treat the internal female reproductive organs.

Another object of the present invention is to provide a method by which antigens or antibodies can be delivered to the uterus so that the internal organs can be treated directly to avoid systemic administration of the antigen or antibody.

Still another object of the present invention is to provide antibodies and antigens incorporated within microparticles which, when deposited in the vagina, can be transported across the the cervix into the uterus by the natrual transport mechanism of the internal reproductive organs.

Briefly, these objects and other objects of the present invention as hereinafter will become more readily apparent can be attained by a method for achieving the passive immunization of the internal female reproductive organs by depositing antibody containing microparticles directly into the vagina and allowing the natural transport mechanism of the internal organs to convey the microparticles across the cervix into the uterus, whereby the antibody is continuously released from the microparticles.

The present invention can also be used to effect the active immunization of the internal organs by using microparticles which contain an antigen. The microparticles employed in the present process contain the antigen or antibody in a matrix which is biocompatible and biologically degradable.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

Figure 1:
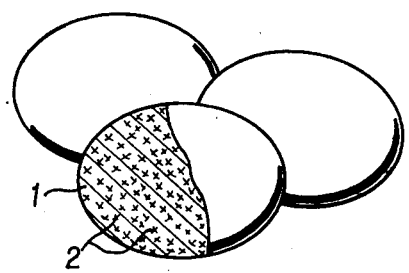
FIG. 1 shows microparticles of a monolithic structure containing a pharmaceutical agent.

The principal object of the present invention is to provide a method for delivering various antibodies or antigens directly to the internal reproductive organs to obviate systemic introduction of antigens or antibodies for the treatment of the reproductive organs. Systemic introduction, in fact, cannot be used as a means for administering many antigens and antibodies into the body for treatment of the reproductive organs. An antibody is defined as any body of globulins that combine specifically with antigens and neutralize toxins, agglutinate bacteria or cells, and precipitate soluble antigens. Antibodies are produced by the specialized cells of the endothelial reticular immune system in response to a challenge by antigens. The antibodies elicited by the challenge are highly specific to the antigen which evokes the repsonse. This characteristic of antibodies has led to their exploitation in clinical medicine for both the diagnosis and treatment of disease. Moreover, both active and passive immunization have been used as a common therapeutic approach for the prevention and treatment of infections diseases in man and animals.

In the past specific antibodies have been employed to retard the growth and proliferation of pathogenic microorganisms in both man and animals as well as to neutralize various bacterial toxins. Antibodies have also been used to control the growth and development of tumors and to modulate the immune system. Other medical uses of antibodies include the neutralization of the biological activity of drugs and hormones and localization of cells that convey unique antigens which may be associated with pathogenic conditions.

There are two basic ways in which the role of antibodies can be stimulated in the body to counteract the effects of antigens. One technique is active immunization while the other is passive immunization. In order to actively immunize a subject, the subject is administered an antigen to induce the formation of endogeneous antibodies. Normally, this technique requires up to two weeks before a sufficiently good level of antibody response is achieved. Because of the delay involved, the active immunization technique imposes limitations for the treatment of infectious diseases which have a short incubation time, for the treatment of a disease actively in progess and for reversing or modifying the effects of drugs, toxins, hormones, and enzymes. Furthermore, if active immunization is to be effective, the subject must have at least a functioning immune system which is capable of repsonding to the invading antigen. Thus, patients suffering from an immunodeficiency disease are precluded from active immunization. Yet a further restriction on the use of active immunization is that the antigens used to immunize a subject must be safe and non-toxic. The use, therefore, of toxic substances in the preparation of vaccines intended for human use is precluded.

The second basic immunization technique is passive immunization whereby antibodies are administered in order to achieve temporary immune protection. Passive immunization has the advantage that the biological effects are immediate and can be effectively used in patients suffering from immunodeficiency diseases. Moreover, active immunization is not limited to the use of non-toxic antigens because animal species can be used as the source for the protective antibodies.

The present invention provides a method of eliciting an active or passive immunization response in the internal reproductive organs of a female subject against an invading antigen as a result of the direct introduction of an antibody or antigen. The direct administration of these biologically active substances is achieved by incorporating specific antibody or antigen in microparticles and then introducing the microparticles of antibody or antigen into the vagina of a female subject and allowing the natural transport mechanism of the internal organs involving in particular the cervix and uterus to convey the microparticles across the cervix into the uterus and eventually into the fallopian tubes. The microparticles release the antibody or antigen over a given period of time thus ensuring the presence of antibody or antigen in the reproduction organs which effectively provides for the active or passive immunization of the subject administered the microparticles.

In the technique of the present invention microparticles containing antigen or antibodies are deposited in the vagina. Transport of the microparticles is controlled by the cyclic changes in the endogeneous ovarian steroid hormones, estradiol and progesterone. During the first 14 days of the menstrual cycle or the follicular or estrogenic phase of the cycle, the ovaries produce estradiol which has a stimulating effect on the cervical muscle contraction. The frequency and amplitude of the cervical contractions during the follicular phase steadily increase from day zero to day 14 at which time ovulation occurs and the cycle enters the lutial phase or progestational phase when the ovaries begin to secrete progesterone. Progesterone has an inhibitory effect on the contractile activity of the cervix or alternatively a muscle relaxing effect on the cervix. The ovarian hormones also exhibit an opposing effect in the cells of the cervix in that estradiol causes an accumulation of secretory products in the cells of the cervix while progesterone promotes the release of these products in the cervical lumen. The interactions described are the mechanism by which changes in the viscosity of cervical fluid occur.

The fluid or mucous of the cervix is dynamic and is an aqueous type of hydrogel. The transport of microparticles as well as sperm is dependent upon the permeability of the cervical mucous to the microparticles as well as the propulsion provided by estrogen induced contractions of the cervix. The most appropriate time for transport of microparticles across the cervix occurs when the uterus exhibits maximum contractile activity and cervical mucous permeability. Accordingly, the greatest rate of transport of sperm or microparticles through the cervix should occur between day 12 and day 16 of the menstrual cycle, although the actual day of ovulation may vary from four to six days in different individuals with some transport occurring in some persons before day 12 of the cycle. Normally, the cervix is not very receptive to transport during the first twelve days of the menstrual cycle as well as between days 16 and 28. Thus, in order to deliver microparticles containing antigen or antibody into the cervix, the microparticles in an appropriate dosage need only to be deposited in the vagina prior to day 16 of the cycle, preferably before day 12 so that full advantage can be taken of the 4 day period at midcycle for transport of the microparticles across the cervix into the uterus.

In a major embodiment of the present invention advantage can be taken of the fact that estrogen and progestin hormones have a transport stimulating effect on the internal organs. Thus, microparticles containing either an estrogen or progestin or both can be introduced into the vagina to regulate the menstrual cycle of a woman who is not cycling regularly or to stimulate the cervix to transport microparticles across the cervix into the uterus and fallopian tubes. Once the microparticles containing cycle regulating hormone are deposited in the vagina, hormone is released by the microparticles and is absorbed by the vagina and/or in the cervix if indeed some microparticles have penetrated into the cervix. The locally absorbed hormone then induces the necessary secretory changes in the endometrium of the cervix and promotes the contractile activity of the cervix necessary for microparticles transport. Once transport activity has begun, the microparticles are conveyed across the cervix into the uterus. From the above discussion it is evident that microparticles containing cycle regulating hormone can be administered to regulate the menstrual cycle and to stimulate transport microparticles containing antigen or antibody across the cervix into the uterus.

The amount of estrogen or pregestin administered via the microparticles should be an amount which, when delivered locally by absorption, is sufficient to regulate the menstrual cycle and to cause the change in the cervix which results in microparticle transport across the cervix. In other words, as the menstrual cycle regulating hormone is absorbed by the tissues of the vagina and indeed the tissues of the cervix if any microparticles have entered into the cervix, the desired regulatory effect is initiated immediately. The desired changes occur in the cervix which promote microparticles transport among which is a gradual increase in the contractile activity of the cervix. The administration of a large dose which results in achieving significant levels of the hormone on a systemic level, i.e. significant concentrations on the blood stream which result in delivery of the hormone to other organs such as the brain and liver in addition to the reproductive organs, should be avoided. Both estrogen and progestin in proper amounts will stimulate transport. However, a progestin at too high a level of concentration will have an adverse effect on microparticle transport because the progestins have a muscle relaxing effect on the tissues of the cervix. However, the adverse effect of the administered progestin can be reversed by the administration of a sufficient concentration of an estrogen via estrogen containing microparticles such as estradiol which as discussed supra induces contratile activity of the tissues of the cervix. Normally, when estradiol is delivered locally by way of the microparticles, the amount of microparticles administered should be sufficient to deliver from 0.1 to 1 mg per day over a 7–14 day period. On the other hand, when progesterone is incorporated in the microparticles, the amount of microparticles administered should be sufficient to deliver from 0.5 to 2 mg per day over a 7–14 day period.

As alluded to above the microparticles of the present invention can provide the feasibility of locally administering a contraceptive agent to the cervix while simultaneously exogenously activating a menstrual cycle in a non-cycling woman by the administration of appropriate ovarian hormone and stimulating the cervix for microparticle transport. Hence, estrogen containing microparticles which also contain the desired antibody or antigen agent can be administered such that estradiol or a synthetic estrogen is released at the cervix for a fourteen day period thus duplicating the first half of the menstrual cycle. When transport of the microparticles occurs across the cervix, antigen or antibody in the microparticles is delivered to the uterus. Fourteen days after administration of the estrogen containing microparticles, progesterone containing micrparticles optionally containing antibody or antigen are then administered. Thus, the complete natural menstrual cycle can be duplicated while providing antibody or antigen protection. It is also apparent that antigen or antibody and estrogen or progestin rather than being incorporated in the same microparticles can be incorporated in separate microparticles and delivered as a mixture so that each biologically active agent is present to deliver its intended function. Of course, it is also within the scope of this invention to deliver microparticles containing estrogen or progestin into the cervix to regulate the cycle and thereafter administer antigen or antibody containing microparticles at the period of the cycle when the cervix is receptive to transport. In the artificially induced cycle maximum transport across the cervix is achieved between days 12 and 16. Since the cycle regulatory hormones are administerd locally in the present technique, effective estradiol activity can be achieved at dosage rates between 0.01 and 0.07 mg per day, while effective progesterone activity can be attained at dosage rates of 0.04 to 0.14 mg per day. Estradiol and progesterone are the regulatory hormones of choice because they are naturally occurring endogenous hormones and therefore present no toxicity problems. However, it is evident that other well known synthetic estrogens and progestins can be employed as substitutes for estradiol and progesterone, respectively. Suitable estrogens include estrone, mestranol, ethinyl estradiol, 2-methoxyestrone, 2-hydroxyestrone and estriol. Suitable progestins include norethindrone, dimethisterone, ethynodiol diacetate, norethynodiol, norethindrone acetate and norgestrone. When the synthetic compounds are employed, the dose employed depends entirely upon the biological potency of the synthetic estrogen or progestin compound.

Microparticles containing antibody or antigen and/or menstrual cycle regulating hormone can be formed in a variety of configurations depending upon such factors as when during menstrual cycle the microparticles are delivered, whether sustained slow release or fast release of drug is desired, whether antigen or antibody is to be administered simultaneously with the menstrual cycle regulating hormone or after administration of the cycle regulating hormone, whether drug release is desired slowly and continually, intermittently or suddenly or the like. In perhaps the simplest situation as shown in FIG. 1 microparticles of a monolithic structure are prepared in which the desired antigen or antibody 2 is distributed throughout a matrix material 1 which is biodegradable and biocompatible. Once the microparticles are deposited in the vagina they begin to slowly deteriorate thereby continuously releasing the desired drug to achieve the desired daily dosage of drug over a prolonged period of time from the time they are deposited in the vagina until well after the microparticles have been conveyed across the cervix and deposited in the uterus. In fact, the transport forces will result in some microparticles being deposited in the fallopian tubes. The term microparticles is used in a generic sense since the particles no matter in what particular configuration or regimen administered do not have to be spherically shaped in the form of microcapsules but can be of an irregular shape. Successful transport of the particles across the cervix is not dependent on the shape of the particles. When microparticles of a monolithic structure are administered, the drug diffuses out of the microparticles by gradual deterioration of the matrix material, by permeation of the drug out of the matrix, or by both mechanisms.

Figure 2:
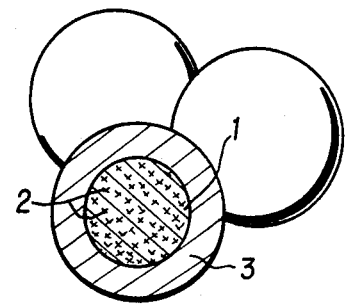
FIG. 2 shows microparticles formed of a core of pharmaceutical agent in a matrix material surrounded by a shell of matrix material.

In another embodiment of the microparticle structure, as shown in FIG. 2, microparticles of a monolithic structure as shown in FIG. 1 are formed as described above. The monolithic microparticles are then further processed such that a wall or outer shell 3 of matrix material free of drug is formed on each microparticle. This type of microparticle configuration is desirable where release of the drug is to be delayed for some period of time after deposition of the microparticles in the vagina. The delayed release of drug obtained by using the above microparticles, for instance, would allow sufficient time for the microparticles to be deposited in the vagina, transported across the cervix and deposited in the urterus before the microparticles deteriorate to the point where the outer shell is essentially eliminated and drug release commences. While the thickness of the outer shell can be varied to any thickness desired, nevertheless, the overall size of the microparticles must be such that the microparticles possess sperm surrogate activity. If the microparticles are of such a relatively large size that they do not have sperm surrogate activity, then the microparticles will not be transported across the cervix and therefore cannot be used.

Figure 3:
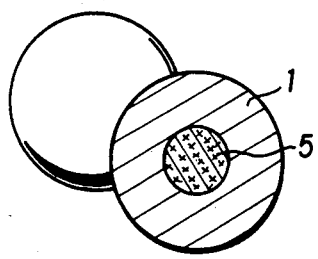
FIG. 3 shows microparticles formed of a core of pharmaceutical agent surrounded by a shell of matrix material.
Figure 4:
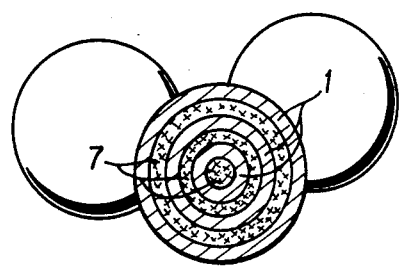
FIG. 4 shows microparticles of an onion-skin structure of alternating layers of matrix material and pharmaceutical agent.
Figure 5:
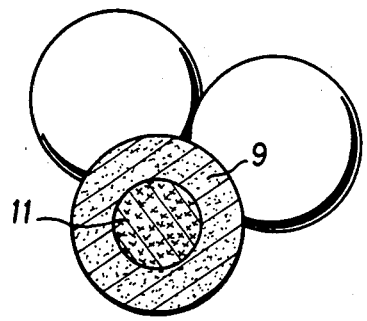
FIG. 5 shows microparticles formed of a core of one particular pharmaceutical agent surrounded by a shell of matrix material containing a second type of pharmaceutical agent.

In still another embodiment of the microparticles as shown in FIG. 3, the microparticles can be designed for the sudden release of a large amount of antibody or antigen. To achieve this purpose the microparticles can be formed such that a core 5 of antigen or antibody is encapsulated in a shell matrix material 1. Microparticles containing a core of drug would be particularly well suited in situations where an endogenous factor for disrupting the outer shell of the microparticles is exploited. For example, the difference in pH of the mucosal fluids in the vagina on the one hand, and the cervix and uterus on the other hand, can be exploited such that deterioration of the outer shell occurs when the microparticles reach the area of the cervix or uterus. In this situation, the acidic pH of the vagina would have little or no effect on the shell of the microparticles. However, when the microparticles are conveyed into the cervix where they are exposed to the neutral pH therein, breakdown of the outer shell would commence eventually resulting in the sudden release of drug. This procedure would be particularly desirable where it is desired to administer a booster response after an individual has already received a primary immunization. Although it is more desirable to have a sustained release of antigen from microparticles of a monolithic structure, for instance, when an individual is to experience primary immunization, a shorter period of drug delivery is satisfactory for boosting the primary immune response.

With regard to passive immunization by the administration of antibody, it would be very desirable when a subject or patient has an acute infection or high concentration of toxin to be able to deliver a substantial amount of antibody quickly to the affected organ(s). By administering microparticles containing cores of antibody, once the microparticles are conveyed into and through the cervix, the antibody will suddenly be released in large quantities to counter the particular disorder. After the initial treatment microparticles could be administered to provide a sustained, lower level release of antibody to continue treatment.

In the treatment of patients for some disorders it is advantageous to be able to administer antigen or antibody in an intermittent fashion. This could be accomplished by the use of microparticles having the configuration shown in FIG. 4 where alternate layers of drug alone or dispersed in matrix material 7 and drug free matrix material 1 are formed in concentric layers. When such microparticles are deposited in the vagina, release of drug does not occur until the outer layer of the microparticles disintegrates. This could delay drug release until the microparticles are conveyed into the cervix and/or uterus. Once the underlying layer is exposed drug release starts and continues until the layer disintegrates or releases the drug. Drug release ceases as the next underlying drug free layer is reached. In this manner intermittent release of the drug is achieved. An example of the applicability of this technique can be found in active immunization where the outermost drug layer releases antigen for a sustained period which is followed by a period for instance of a week or two, in which no drug is released. After the non-drug containing layer disintegrates, a second period of antigen release starts. In this manner one could in a single administration of microparticles provide a primary immunization dose followed by a booster dose.

When it is desired to not only convey an antigen or antibody to the uterus through the cervix but also administer cycle regulatory hormone in order to activate or regulate the natural transport mechanism, it is possible to administer microparticles of a monolithic structure as shown in FIG. 1 in which both antigen or antibody and cycle regulating hormone are dispersed through a matrix material. In this manner, once the microparticles are deposited in the vagina, release of both hormone and antigen or antibody starts and eventually the microparticles are conveyed across the cervix into the uterus. A perhaps more selective regimen of administration could be provided by microparticles which have an outermost matrix layer containing cycle regulatory hormone and an inner core of matrix material containing antigen or antibody. When such microparticles are administered, the sustained release of cycle regulatory hormone occurs, and when the cervix is receptive to transport, the microparticles are transported across the cervix into the uterus. Release of the antigen or antibody will occur in the cervix or uterus as the underlying antigen or antibody core of the microparticles is exposed. FIG. 5 shows microparticles of the structure discussed above in which outer cycle regulatory hormone containing layer 9 encapsulates inner antigen or antibody containing core 11. The antigen or antibody alone can constitute the core of the microparticles or the antibody or antigen can be dispersed in matrix material to form core 11. However, outer layer or shell 9 is formulated by dispersing a menstrual cycle regulatory hormone in a matrix material.

From the above discussion it is evident that antibody or antigen alone or in combination with a cycle regulatory hormone can be incorporated in microparticles in a variety of configurations depending upon how the drug or drugs are to be released. Moreover, while multi-layered microparticles such as the types shown in FIGS. 2, 4 and 5 are normally formed of a single type of matrix material, it is possible, if not desirable under some circumstances, to formulate contiguous layers of the microparticles from different matrix materials. Still further it is possible that under some circumstances, it may be desirable to deliver more than one antibody or antigen to the internal reproductive organs to treat more than one condition. Thus, for instance, monolithic microparticles could be prepared and delivered containing two different antibodies to passively treat two different diseases. In fact, it may be desirable under some circumstances to actively immunize a patient against one disorder and simultaneously passively immunize the patient against a second disorder with antigen and antibody delivered in the same microparticles. Of course, when more than one antigen and/or antibody is combined in one microparticle where they may be in contact and not in different layers of a microparticle, they must not react with each other. A very similar situation exists where it may be desirable to include more than one type of estrogen or progestin in the same microparticle. The above embodiments only describe several of many possible microparticle configurations.

With regard to the physical size or shape of the microparticles, the microparticles can assume any possible shape ranging from ordered shapes such as spherical or oval to irregular shapes. The shape of the microparticles is not a factor in microparticle transport.

The size of the microparticles is important insofar as the microparticles must possess sperm surrogate activity such that they can be conveyed by the natural transport mechanism of the reproductive organs upward from the cervix into the uterus and eventually into the fallopian tubes. If the microparticles are too large, they will cause contractions of the cervix which will expel the microparticles. Microparticles which are too small will not be conveyed upward into the internal reproductive organs. Usually, the microparticles range from 10 to 100 μm, preferably 20 to 70 μm, most preferably 20–60 μm. While the mechanism of microparticle transport is not known precisely, several factors are known which are important for transport. The cervical mucous is a type of aqueous hydrogel which is dynamic in that the viscosity and flow characteristics range during the monthly cycle of the reproductive organs. If transport of the microparticles is to be achieved, the matrix material of the microparticles must be compatible with the cervical mucous. The compatibility of the microparticles is a function of not only the chemical nature of the matrix material of the microparticles, but also the size of the microparticles. The microparticles must be miscible with the cervical mucous. Transport of the microparticles across the cervix, just as in the case of the sperm, is achieved only when the cervix is prepared to transport the microcapsules. Accordingly, the microparticles containing antigen or antibody must be deposited in the vagina when the cervix is ready to transport the microparticles. Once the cervix is ready for transport, synchronized muscle contractions of the cervis propel the microparticles into the uterus where eventually some of the microparticles are conveyed through the uterus into the fallopian tubes, although the important objective of the invention is that the microparticles should cross through the cervix into the uterus. The muscle contractions of the cervix are controlled by the natural release of hormones at the appropriate time of the monthly female cycle which as discussed above is at midcycle. Alternatively, as discussed at length above, the transport mechanism can be stimulated by the administration of cycle regulatory hormone.

In the preparation of the antibody or antigen containing microparticles essentially any known antigen or antibody can be incorporated in the microparticles although those of particular use in the treatment of conditions and diseases of the internal reproductive organs are preferably used. Antibodies of the same type have the same biochemical structure regardless of what antigen they react with. Therefore, the same process can be used to incorporate any type of antibody in microparticles regardless of their specificity. Suitable types of antigens which can be incorporated in the present microparticles include bacterial and viral pathogens of man and animals, however, enzymes and other biological factors involved in the reproductive process can also be used. Suitable pathogenic antigens include *Neisseria gonorrhea, Mycobacterium tuberculosis,* Herpes virus (humonis, types 1 and 2), *Candida albicans, Candida tropicalis, Trichomonas vaginalis, Haemophilus vaginalis,* Group B *Streptococcus ecoli, Microplasma hominis, Hemophilus ducreyi, Granuloma inguinale, Lymphopathia venereum, Treponema pallidum, Brucella abortus, Brucella melitensis, Brucella suis, Brucella canis, Campylobacter fetus, Campylobacter fetus intestinalis, Leptospira pomona, Listeria monocytogenes, Brucella ovis,* Equine herpes virus 1, Equine arteritis virus, IBR-IBP virus, BVD-MB virus, *Chlamydia psittaci, Trichomonas foetus, Toxoplasma gondii, Escherichia coli, Actinobacillus equuli, Salmonella abortus ovis, Salmonella abortus equi, Pseudomonas aeruginosa, Corynebacterium equi, Corynebacterium pyogenes, Actinobaccilus seminis, Mycoplasma bovigenitalium, Aspergillus fumigatus, Absidia ramosa, Trypanosoma equiperdum, Babesia caballi, Clostridium tetani.*

Suitable examples of enzymes that may be involved in the reproductive process include ribonuclease, neuramidinase, trypsin, glycogen phosphorylase, sperm lactic dehydrogenase, sperm hyaluronidase, adenossine-triphosphatase, alkaline phosphatase, alkaline phosphatase esterase, amino peptidase, trypsin chymotrypsin, amylase, muramidase, acrosomal proteinase, diesterase, glutamic acid dehydrogenase, succinic acid dehydrogenase, beta-glycophosphatase, lipase, ATP-ase alphapeptate gamma-glutamylotrans peptidase, sterol-3-beta-ol-dehydrogenase, DPN-di-aprorase.

Suitable examples of hormones acting as antigens include human chorionic gonadotrophin hormones, human placental lactogen, progesterone, estradiol and the like. Suitable antigens include those known as embryonic cellular antigens which occur on the cellular surface of the trophoblast and are unique to the trophoblast. In addition to the above mentioned pathogens, mixture of pathogens which can infect the female reproductive organs also can be incorporated in microparticles. Stated simply any pathogen can be used to produce a vaccine which could then be used to immunize the cervix, uterus and fallopian tubes by the present technique.

Examples of antibodies for passive immunization which can be incorporated in microparticles include those which correspond to all of the above described antigens which are effective for active immunization.

When the microparticles of the present invention are administered to a subject, they are administered in an amount sufficient to elicit an effective level of response over a period of time desired. For treatment of the cervix, uterus and/or fallopian tubes a suitable dose range for an antigen for the role of primary active immunization would be 0.5 to 1 mg of antigen per day over a 7–14 day period. The dosage range required for a booster immunization would vary from 0.5 to 1 mg per day over a 24 hour time span. With regard to passive immunization via antibody administration, the weight of antibody administered does not necessarily directly relate to the therapeutic effect realized. The important factor in terms of dosage for passive immunization is the titer of the antibody or the biological potency. The titer of an antibody refers to the maximum dilution of the antibody which elicits an effect in a test situation. Two different preparations of antibody are not equally comparable on a weight basis because they have different biological potencies. An immunological titer of 1:500 is the minimum biological potency for any antibody to be administered by the process of the present invention. Moreover, the rate at which the immumoglobulin or antibody should be delivered to the cervix, uterus and fallopian tubes should not exceed 0.1 mg of antibody per day. Any dose rate less than this level which is effective in eliciting a therapeutic response is acceptable. Dosage rates greater than this level are unacceptable because the larger dose may cause a sensitization reaction against the antibody. That is, if the dosage rate is too great, the passively administered antibody might function as an antigen thereby stimulating the production of antibodies in the host that would react with the administered antibodies.

As described above, the matrix material in which the antigen or antibody is incorporated is an important consideration. Three factors predominate in the selection of a matrix material which are the biocompatibility of the matrix material with the mucosal fluids, the permeability of the matrix material and the ability of the matrix material to degrade biologically by a mechanism such as hydrolysis so that no matrix material residues remain after transport and deterioration of the microparticles in the uterus and fallopian tubes. The release of antigen or antibody from the microparticles may occur by diffusion of the agent through the entrapping matrix material or by erosion of the matrix material or by a combination of both factors. Suitable polymers as matrix materials include polyglycolic acid, polylactic acid, as well as copolymers of glycolic and lactic acid, and glycerol mono- and distearate. The preferred matrix materials, however, are polylactic acid and polyglycolic acid. The aliphatic polyesters described above degrade biologically by hydrolysis under physiological conditions and are converted to monomeric glycolic and lactic acids. The rate of degradation of the polymer in the body preferably occurs as soon as possible after the drug is released and is related to the rate of hydrolysis of the ester linkages which is, in turn, related to the surface area of the microcapsule or device, the crystallinity of the polymer, and the inherent hydraulic stability of the polyester.

The molecular weight of the particular polymer chosen is not a critical factor in the manufacture and use of the microcapsules. While an increase in the molecular weight of the polymer may gradually retard the rate of release of therapeutic agent(s) from the microcapsules and thus affect the dosage level administered, these factors may easily be compensated for by determining the rate of release of therapeutic agent(s) from the microparticles by in vivo or in vitro measurements and then adjusting the amount of microparticles administered in view of the results obtained from the release measurements.

The antigen or antibody containing microcapsules can be conveniently prepared by any well known procedure used in the past for the preparation of microparticles containing a pharmaceutical material. While the amount of antigen or antibody, and cycle regulatory hormone, if it is to be present, is not critical, normally, the microparticles contain from about 10 wt.% to 60 wt.%, preferably 10 wt.% to 50 wt.%, most preferably 10 wt.% to 25 wt.% of antibody or antigen. The methods selected for preparing the microparticles are not critical although they will vary principally depending upon the type of microparticles to be prepared, i.e. whether the microparticles are to be monolithic, or manufactured such that a core of pharmaceutical material is surrounded by a wall of encapsulated matrix material or manufactured in a manner such that an onion-skin type of structure results with alternating layers of matrix material and pharmaceutical material alone or in a matrix material.

In the manufacture of the microparticles containing antigen or antibody and/or a menstrual cycle regulatory hormone, any conventional method of forming the microparticles can be used. The selection of a particular method chiefly depends upon the technical requirements of the matrix material and the particular manner in which the microparticles are intended to be used.

Generally, microencapsulation processes can be classified according to the three principal types of: (1) phase-separation methods including aqueous and organic phase separation processes, melt dispersion and spray drying; (2) interfacial reactions including interfacial polymerization, in situ polymerization and chemical vapor deposition; and (3) physical methods, including fluidized-bed spray coating, multi- and single-orifice centrifugal coating, electrostatic coating and physical vapor deposition.

Phase separation method, as the term implies, rely on differential solubility characteristics that cause a wall- or shell-forming matrix material to separate from solution or suspension and deposit around particles or droplets of the therapeutic agent(s) to be encapsulated. The separation itself may be brought about physically, as by the addition of a non-solvent or by a change in temperature, or chemically, as by a change in pH.

An organic phase-separation process usually employs a dispersion or an emulsion of the therapeutic agent(s) in a solution or a high-molecular-weight polymer in an organic solvent. To this mixture is added a non-solvent or liquid polymer that causes the high-molecular-weight polymer to separate from solution and collect as a shell around the suspended therapeutic agent(s). The shell, still swollen with solvent, is then hardened by a further addition of non-solvent or by some other process that strengthens the shell and improves the barrier properties.

Typically, an aqueous solution or suspension of a lipophobic antigen or antibody and/or menstrual cycle regulatory hormone is added to a non-aqueous solution of a suitable matrix polymer, and the mixture is agitated to cause the formation of a water-in-oil emulsion. Depending upon its solubility in water, the agent may be present at a concentration of 5 to 50% in the aqueous phase, which may be 5 to 20% by weight of the total mixture. The external organic phase may contain 5 to 10% of the matrix polymer. Usually, however, the ratio of agent in the internal phase (aqueous solution or suspension) to polymer is 2:1 to 1:4. The polymer must be a good film-former; that is, it most possess adequate strength and toughness.

An aqueous phase separation process employs a dispersion or an emulsion of a water-insoluble therapeutic agent(s) in an aqueous solution of dispersion of a polymer. The polymer is caused to separate as gel particles; these collect around the therapeutic agent to form a shell; the shell is hardened; and the microparticles are isolated. In the conservation process, which is the most common of the aqueous phase-separation processes, the water-insoluble therapeutic agent, which may be in the form of particles or droplets, is usually dispersed in an aqueous sol of a hydrophilic colloid which becomes ionized in water; a second sol of opposite charge is added; and the mixture is caused to gel by a dilution with water, an addition of salt, an adjustment of pH, or a change in temperature, or by combination of these. Appropriate conditions of conservation are usually determined experimentally, because the various polymers, possible for use, differ significantly in physical and chemical properties according to source and method of isolation or preparation. A region of coacervation is determined by combining solutions or sols of two polymers at various concentrations, temperatures and levels of pH, and observing the conditions required for gelation. From these determinations can be drawn a ternary phase diagram, showing the area of compatibility and the region of coacervation, at a given temperature and pH. The changes in concentration, temperature or pH to effect gelation will then become apparent.

Each preparation of microparticles requires carful control of conditions, and somewhat different conditions are required for various therapeutic agents. The degree of agitation, for example, affects the size of emulsion droplets, and the surface properties of the droplets may require alterations in the procedures to insure deposition of matrix material about the droplets and to minimize formation of particles not participating in microencapsulation. The volume of water added in the dilution step is not critical, but generally larger volumes are required to maintain a stable emulsion when larger droplets are encapsulated.

The above phase separation can be adapted to an alternate technique in which the first step of forming a stable emulsion or suspension of the medicinal or therapeutic agent is accomplished by dispersing the agent in a solution of the matrix material. Thereafter, the emulsion is added dropwise to a non-solvent with stirring to precipitate the polymer coating material to form microparticles.

Another type of phase separation technique is the melt-dispersion microencapsulation technique. This method can be used with a wide variety of medicinal or therapeutic agents. Usually a heat-liquifiable, waxy coating material, preferably of a low-melting wax such as glycerol distearate is suspended in an inert liquid such as a silicone oil or a fluorocarbon in which neither the wax nor the material to be encapsulated is appreciably soluble. The mixture is heated and stirred vigorously to melt and emulsify the wax. The therapeutic agent which has been powdered and screened to the desired size range, and the waxy coating material are dispersed with high shear agitation, and the liquefied wax coats the therapeutic agent to form the waxy liquid-coated microparticles. Thereafter, the formed microparticles ae solidified by continued agitation which cools the particles. The microparticles are then isolated by filtration and dried as described earlier.

The second major method of forming the microparticles is by interfacial microencapsulation which involves bringing two reactants together at a reaction interface where polycondensation of the reactants, usually monomers, occurs to form a thin, insoluble polymeric film. One technique of establishing the interface for the encapsulation process is the dispersion or emulsification of the therapeutic agent with one of the reactants which form the condensation polymer in a continuous phase containing the second reactants.

The third major category of encapsulation techniques which is especially applicable to a variety of medicinal or therapeutic agents and coating materials is physical microencapsulation. The physical microencapsulation techniques are characterized by the continuous envelopment of particles or droplets of a medicinal or therapeutic agent in a fluid film, as a melt or solution of the coating material, in an apparatus containing coaxially or sequentially-spaced orifices. Thereafter, the fluid coating is hardened by a standard cooling technique or by solvent evaporation.

Among the physical methods for microencapulsation are those that involve the passage of liquid or solid core material through a liquid matrix material. The stream is disrupted by some means to cause the formation of liquid-coated droplets or particles, and the resulting particles are cooled or otherwise treated to solidify the shell material. For example, an aqueous solution of a therapeutic agent is aspirated into a rapidly flowing stream of molten glycerol disterate, and the mixture is ejected through a fine nozzle. On emergence from the nozzle, the liquid stream disintegrates into droplets, each consisting of an aqueous core surrounded by liquid wax. As these fall through air, the shells cool and solidify, and microparticles result. In another version of this process, the impelling force is supplied by a rotating member, which ejects the core material centrifugally through the shell-forming liquid.

The variations of these and other processes of microencapsulation are many. As is readily apparent to those skilled in the art, no one process nor any single set of conditions is applicable to all therapeutic agents, but instead a useful process is chosen and the conditions optimized to achieve the desired results with a specific agent.

Microcapsules containing medicinal or therapeutic agents can be delivered in the vagina by a variety of methods. The preferred method is to incorporate a fixed number of microcapsules into a container designed for easy hand insertion into the vagina. The insertion container should be made of a biodegradable material that dissolves within minutes after placement in the vagina, thus, releasing the microcapsules. Pharmaceutical type gelatin capsules can be conveniently used as a delivery system for the microcapsules. The dose level can be varied by increasing or decreasing the number of microcapsules in the delivery device. Of course, any number of other methods of variations, or this preferred method might be used. For example the microcapsules could be molded into a solid vaginal suppository by using an appropriate suspension medium such as gelatin. Creams, jellies, foams, or liquids might be used as a suspension medium for microcapsules. Preparations of this type could be placed in the vagina using a loadable syringe or some type of pressurized vaginal inserter. A variety of different types of applicators for administering pharmaceutical agents to the vagina and rectum are in common use. These consist of two parts; a nozzle design for easy insertion into the vagina, and a hand held implement used to project the preparation into the vagina. Syringes, squeeze bulbs, squeeze tubes and aerosol containers are examples of implements that can be used to generate the force necessary to propel the preparation into the vagina.

Vaginal suppositories offer the simplest, most direct method of application. The microparticles are inserted into the lower half of a preformed gelatin shell. The margin of the shell is then moistened with water and the upper half of the shell is joined to the lower half to complete formation of the suppository Four, eight and twelve grain gelatin capsules can be used in this manner depending upon the dosage of microcapsules desired. Suppositories of other materials such as jellies, creams, foams or aerosols can also be used as the delivery system for microcapsules. The dose can be strictly regulated by including a fixed number of microcapsules in the suppository preparation, and the carrier device can be applied by hand. Another advantage is that by using a hollow container such as a gelatin capsule, special suspension media which might adversely affect the migration of the microcapsules are not needed.

The primary limitation for the generation of passive immunization in a subject by the administration of antibodies in clincal medicine is that antibodies produced in animals quite often cause serum sickness or anaphylaxis when injected into human recipients. However, the local delivery technique of the present invention in which microencapsulated antibodies are transported into the internal female reproductive organs circumvents this problem because not only are smaller dosages of antibodies required, but also systemic administration of antibodies is avoided. It is acknowledged that the use of humans as antibody donors can circumvent this problem. However, human donors cannot be used safely when immunization affects their own physiology or necessitate the use of antigens which are toxic. A distinguishing feature between active and passive immunization is that the natural elimination of passively administered antibodies from a subject renders this approach temporary and reversible, whereas active immunization of a subject is usually permanent and non-reversible.

Any type of reaction between administered antibody and antigen within the local environment of the internal reproductive organs to elicit a passive immunization response is within the scope of the present invention. For example, antibodies effective against any type of bacterial or viral pathogen can be used in the local treatment of infections in the vagina, cervix, uterus and fallopian tubes. Similarly, antibodies produced against sperm, egg, products of conception and biological factors in the reproductive fluids including hormones such as HCG and enzymes can be employed to prevent pregnancy. One potentially very important application of the present invention is a method of treating the veneral disease, gonorrhea, which is caused by the microorganism, *Neisseria gonorrhea*. This microorganism lives and proliferates in cavities in the cervix, uterus and fallopian tubes of infected women. Thus, the present invention provides a technique of generating a passive immunization in an infected host against this disease. It is noteworthy to emphasize at this point that there is no known method of immunization against gonorrhea because standard methods of immunization are not effective since these techniques induce systemic antibodies which are not secreted into the various parts of the internal female reproductive organs. Other diseases which can be treated by the passive immunization technique of the present invention include syphillis, simplex herpes viral infections, yeast infections, trichomoniasis bacterial infections and the like.

Still another aspect of passive immunization within the scope of the present invention is the use of antibodies to reduce female fertility. The human preimplantation embryo produces and secretes a hormone called chorionic gonadotrophin hormone (HCG), which is necessary for implantation of the embryo into the uterus. It is known that antibodies against HCG neutralize the functions of this hormone and prevent implantation of the embryo from occuring. Accordingly, antibodies effective against HCG can be introduced into the internal female reproductive organs by the the technique of the present invention to prevent pregnancy. This technique can be extrapolated to the use of antibodies against sperm, egg, products of conception and a wide variety of enzymes and hormones which can be found in the fluids of the reproductive tract.

In some instances active immunization is more advantageous than passive immunization with an obvious example being active immunization for permanent protection against infectious diseases. Thus, when an antigen is incorporated within microparticles which can be delivered to the cervix, uterus and fallopian tubes, the delivered antigen induces the formation and secretion of specific antibodies by these organs. The secreted antibodies not only provide the desired immunological effect, but also are structurally and fundamentally unique from the type of antibody produced in response to systemic immunization. Systemic antibodies are not secreted by the reproductive organs, and it is for this reason that systemic immunization is not an effective way of generating antibodies in the fluids of the cervix, uterus and fallopian tubes. Thus, standard methods of immunization are not effective in the prevention of infections of the internal female organs or for controlling fertility. In the present invention, on the other hand, not only are antigens delivered directly to the internal female organs, but the mode of release of antigen from the microparticles varying from a sudden release to a sustained release ensures that the antigen can be administered as desired thus ensuring sensitization.

In a typical example of active immunization, antigens from the microorganism, *Neisseria gonorrhea*, for instance, are incorporated in a polymer such as polylactic acid. The microparticles are then administered into the vagina of a subject where they are then conveyed across the cervix into the uterus. The microparticles release antigen at the desired rate perhaps in the cervix as the microparticles are conveyed into the uterus. The antigen sensitizes the secretory tissues of the internal organs which respond by producing protective antibodies. The secreted antibodies form a protective fluid coating along the surfaces of the internal organs which protects the subject against an invasion and infection of *N. gonorrhea* microorganisms. The same technique can be employed to immunize a subject against other bacterial and viral infections of the internal female reproductive organs.

Another aspect of active immunization pertains to fertility. In this case, sperm antigens are delivered by transport of antigen containing microcapsules into the cervix, uterus and fallopian tubes. The antigen which is slowly released over a sustained period of time, stimulates the secretory tissues of the organs to secrete protective antibodies in the fluid layer which coats the internal organs which essentially are the cervix, uterus and fallopian tubes. After copulation and deposition of sperm in the vagina, antibodies in the cervical mucous cause agglutination of the sperm in the cervix and prevent further transport of the sperm into the uterus. Antibodies against sperm also inactivate sperm by techniques other than agglutination.

There are many recognized advantages to fertility control by immunization. The most obvious benefit is that immunization with an anti-fertility vaccine could provide sustained fertility control. An important advantage of the local administration technique of the present invention is that the vaccine could be self-administered at low cost. Recently, several antigens have been isolated and identified which are unique to the reproductive process which will induce an anti-fertility immune response. These antigens include those of the blastocyst, the ovum, the sperm, non-hormonal placental antigens and trophoblastic hormonal antigens.

The present concept of basing fertility control upon the local and direct administration of antigens to the internal female reproductive organs is founded on the assumption that a high concentration of antibodies within the reproductive tract may be more efficacious and safe for inhibition of sperm or blastocyst vitality than systemic immunization. It is believed that anti-sperm or anti-trophoblastic hormone immunity interferes with the reproductive process in the female genital tract before or during embryonic implantation. In fact, it is known that when HCG antigens are administered systemically, systemic antibodies may cross-react with other tissues of the body thereby giving rise to detrimental side-effects. The risk of the systemic side-effects precludes the use of this method for controlling fertility in humans. However, if indeed local immunity of the reproductive organs can be increased in the absence of a systemic immune response, then many of the complications associated with systemic immunization can be avoided. Furthermore, the present invention has the advantage that cyclic overdosing and underdosing which are inherent in conventional methods of administering drugs can be obviated by the sustained release of antigen or antibody from microparticles. Thus, the present technique affords a means for effecting a pharmacological response with a minimum dose of drugs.

Having now generally described the invention, a more complete understanding can be obtained by reference to certain specific examples which are included for purposes of illustration only and are not intended to be limiting unless otherwise specified.

EXAMPLE 1

Preparation of Progesterone Containing Polylactic Acid Microcapsules

A 2.5 g amount of progesterone and 10.0 g of d,l-polylactic acid were dissolved in 38 g of methylene chloride. The resulting viscous solution was poured into a 250 ml kettle containing 120 ml of a 5 wt.% aqueous polyvinylalcohol solution. The dispersion obtained was stirred at about 2000 rpm until a stable emulsion had formed with the droplets being in the range of 50 to 100 $\mu$m in diameter. A vacuum was applied to the emulsion until it began to foam and then the rate of stirring was reduced to 600 rpm. After two hours, most of the methylene chloride had evaporated. Moreover, continuous stirring was not required to prevent the embryonic microcapsules from agglomerating. Thereafter, the emulsion was centrifuged, the aqueous polyvinylalcohol solution was decanted and the microcapsules were resuspended in 150 ml of deionized water. For about 18 hours thereafter a vacuum was continually applied to the stirred aqueous suspension. Thereafter, the suspension was centrifuged and the microcapsules obtained were washed with water and then collected by vacuum filtration. The microcapsules were dried at room temperature under a hard vacuum overnight, and then they were sieved whereby a fraction ranging between 43 and 61 $\mu$m was obtained. By this procedure microcapsules containing 22±1.5 wt.% progesterone were obtained.

EXAMPLE 2

The procedure of Example 1 was followed to the extent that the ingredients were mixed and stirred in the aqueous polyvinylalcohol. A vacuum was applied to the stirred dispersion and after about 2 hours, when 90 wt.% of the solvent had been removed, the procedure was interrupted. The suspension was centrifuged and the microcapsules were obtained after decantation. The microcapsules were resuspended in deionized water which did not contain a dispersing agent. A vacuum was reapplied to the suspended microcapsules and the procedure was continued to completion. By this technique the encapsulation efficiency was 100%.

EXAMPLE 3

Preparation of Progesterone containing Glycerol Monostearate Microcapsules

A 1.0 g amount of progesterone was added to 4 g of molten glycerol monostearate and a portion of the molten mixture was poured into the reservoir of a melt sprayer and heated to 167° C. The flow of nitrogen into the device to effect cooling was 60 liters per minute, while the flow of nitrogen into the sprayer to aerosolize the molten mixture was adjusted to the maximum rate of 5.75 liters per minute. The aerosol was sprayed intermittently, and microcapsules were collected and sieved, whereby a size fraction ranging between 43 and 61 μm was collected. The microcapsules produced by this procedure were spherical and contained a 20 wt.% theoretical loading of progesterone.

EXAMPLE 4

A. Preparation of Antigen Containing Microcapsules

An amount of 1.5 g to 2.5 g of a poly (glycolide-lactide) excipient was dissolved in approximately 100 g of methylene chloride. The copolymer comprised a 50:50 mole ratio of glycolide to lactide. The copolymer solution was placed in a 200-ml Bantamware resin kettle equipped with a true-bore stirrer and a 1.5 inch teflon turbine impeller driven by a Fisher "StediSpeed" motor. To this solution was added 0.5 g of an aqueous dispersion of pneumococcus type-III antigen, 0.05 g of an aqueous solution of Herpes simplex antigen or a solution prepared by dissolving 0.15 to 0.30 g of Anti-β-hCG cow antibody in approximately 0.75 g of deionized water. During the addition of the antigen or antibody material, the contents of the resin kettle were stirred at 2100–3000 rpm to form a water-in-oil emulsion. The water micro droplets which formed contained dissolved biological agent and had particle size diameters ranging from 5–60 μm. Stirring of the emulsion was continued and 40–50 ml of silicone oil (Dow Corning 200, 350 cs) was pumped into the resin kettle at a rate of 1–2 ml/min. The silicone oil promoted copolymer phase separation because of copolymer-polymer incompatibility. The copolymer was deposited as droplets of solvent-swollen copolymer onto the surface of the water microdroplets. As more silicone oil was added, more copolymer droplets accumulated until they coalesced to form a continuous film around the water micro droplets. The copolymer film was then hardened by pouring the contents of the resin kettle into a beaker containing about 2000 ml of heptane stirred at 600–1000 rpm with a 2.5 inch stainless steel impeller. This process hardened the microcapsules since heptane is a non-solvent for the copolymer and a solvent for methylene chloride and silicone oil. The heptane extracted methylene chloride from the solvent-swollen walls of the microcapsules, and washed the silicone oil from the surface of the microcapsules. After being stirred in heptane for about 30 minutes, the microcapsules were collected and washed several times with more heptane to remove residual quantities of methylene chloride and silicone oil. The hardened microcapsules were then isolated by vacuum filtration through a Buchner funnel and Whatman number 41 filter paper, and were dried for about 24 hours in a vacuum chamber maintained at room temperature. By this technique free flowing particles having diameters ranging from 10 to 90 μm were obtained. In this manner three batches of microcapsules were prepared within the size range of 10–90 μm of which the first batch (microcapsule system 1) contained the antigen of pneumococcus, type III, the second batch (microcapsule system 2) contained the antigen from Herpes simplex virus, and the third batch (microcapsule 3) contained the protein antigen or antibody.

B. Treatment Of Test Animals

The following animal experiments were conducted to demonstrate the utility of microcapsule systems 1, 2 and 3 in immunizing the internal female reproductive organs. For these experiments adult female rabbits were used; the standard animal model for immunological studies. Five rabbits were assigned to each of three experimental groups and prior to treatment, blood samples and washings from the vagina of each rabbit were obtained. The blood serum and vaginal washes from each animal were tested for the presence of antibodies against pneumococcus, type III antigen, Herpes simplex virus antigen, and Bovine IgG. The serum and vaginal washings from each rabbit were also tested for immune reactivity against the β sub unit of hCG. Only rabbits which exhibited negative results in each of the tests were selected for inclusion in the tests of the present invention. Standard immunological tests were used for demonstrating the existance of antibodies against the bacteria, virus and protein, and for the demonstration of antibodies which react with the β sub unit of hCG.

Each of the adult female rabbits was vaginally administered a 5 mg quantity of a batch of microcapsules obtained from microcapsule system 1, 2 or 3. Five rabbits were treated with each of the three different systems. Two weeks following treatment, vaginal washes were obtained from the rabbits and tested for the presence of antibodies against pneumococcus, type III bacteria (treatment group 1), Herpes simplex virus (treatment group 2), and Bovine IgG (treatment group 3).

The results of the experiments are shown in Table 1 below. The table shows that the pretreatment vaginal wash samples from all fifteen rabbits tested contained no demonstrable antibody against pneumococcus, type III bacteria, Herpes simplex type virus or Bovine IgG. The table further shows that following treatment by intravaginal insertion of 5 mg of microcapsules containing pneumococcus, type 3 bacteria, the post-treatment vaginal washes from rabbits 1-5 exhibited positive titers against pneumococcus, type III bacteria with negative titers against Herpes simplex virus and Bovine IgG. he vaginal washes obtained from rabbits 1-5 also lack demonstrable immunological reactivity against the β sub unit of hCG. The results clearly show that rabbits 1-5 responded to the intravaginal challenge with microencapsulated pneumococcus, type III bacteria by providing antibodies against the bacterial antigens.

With respect to rabbits 6-10, the vaginal washes from these animals exhibited negative titers to all three antigens and no demonstrable immunological activity against hCG. The post-treatment vaginal washes from rabbits 6-10 exhibited positive antibody titers against Herpes simplex virus and negative titers against pneumococcus, type III and Bovine IgG. None of the samples from the rabbits contained any demonstrable immunological activity against the β sub unit of HCG. The results clearly indicate that intravaginal installation of microcapsules containing Herpes simplex virus antigen caused immunization against Herpes simplex virus.

The pretreatment vaginal washes from rabbits 11-15 contained negative antibody titers against pneumococcus, type III, Herpes simplex virus, and bovine IgG and lacked demonstrable immunological reactivity against the beta subunit of hCG. The post-treatment samples had positive titers against bovine IgG, and negative titers against pneumococcus, type III bacteria and herpes simplex virus. It is significant to note that the post-treatment vaginal washes in rabbits 11-15 also contained demonstrable antibody titers against the beta subunit of hCG. This last example illustrates two different applications of the vaginal microcapsule system. On the one hand it demonstrates that the system provides an effective method for the delivery of a protein antigen; in this case, bovine IgG, the results being positive titer against the bovine IgG. The protein in this example is an antibody which has its own immunological reactivity. The demonstration of this antibody in the post-treatment vaginal wash illustrates the use of the microcapsule system for the delivery of antibodies; thus, establishing the utility of the system for passive immunization.

TABLE I

SUMMARY OF RESULTS

| Rabbit Number | Treat. System Number | Bacteria Pneumococcus Type 3 Pre-treat. | Bacteria Pneumococcus Type 3 Post-treat. | Virus Herpes Simplex Pre-treat. | Virus Herpes Simplex Post-treat. | Protein Bovine IgG Pre-treat. | Protein Bovine IgG Post-treat. | Antibody Anti-hCG Pre-treat. | Antibody Anti-hCG Post-treat. |
|---|---|---|---|---|---|---|---|---|---|
| 1 | 1 | − | + | − | − | − | − | − | − |
| 2 | 1 | − | + | − | − | − | − | − | − |
| 3 | 1 | − | + | − | − | − | − | − | − |
| 4 | 1 | − | + | − | − | − | − | − | − |
| 5 | 1 | − | + | − | − | − | − | − | − |
| 6 | 2 | − | − | − | + | − | − | − | − |
| 7 | 2 | − | − | − | + | − | − | − | − |
| 8 | 2 | − | − | − | + | − | − | − | − |
| 9 | 2 | − | − | − | + | − | − | − | − |
| 10 | 2 | − | − | − | − | − | − | − | − |
| 11 | 3 | − | − | − | − | − | + | − | + |
| 12 | 3 | − | − | − | − | − | + | − | + |
| 13 | 3 | − | − | − | − | − | + | − | + |
| 14 | 3 | − | − | − | − | − | + | − | + |
| 15 | 3 | − | − | − | − | − | + | − | + |

Having now fully described this invention, it will be apparent to one of ordinary skill in the art that many changes and modifications can be made thereto without departing from the spirit or the scope of the invention as set forth herein.

What is claimed as new and intended to be secured by Letters Patent is:

1. Anti-B-HCG containing microparticles for the immunization of the internal female reproductive organs, said microparticles containing a biologically effective amount of anti-B-HCG incorporated in a matrix material which is biocompatible and biologically degradable, said microcapsules being capable of being transported after deposition in the vagina by the natural transport mechanism of the internal female reproductive organs across the cervix into the uterus wherein immunization is effected within said internal female organs, said microparticles having a diameter of from 10 to 100 μm.

2. The anti-B-HCG containing microparticles of claim 1, wherein the said microparticles have a diameter of from 20 to 70 μm.

3. The anti-B-HCG containing microparticles of claim 1, wherein the said microparticles have a diameter of from 20 to 60 μm.

4. The anti-B-HCG containing microparticles of claim 1, wherein the said microparticles comprise a central anti-B-HCG containing core surrounded by an outer shell of matrix material free of anti-B-HCG.

5. The anti-B-HCG containing microparticles of claim 4, wherein said outer shell of the microparticles is resistant to the acidic pH environment of the vagina and susceptible to breakdown when exposed to the neutral pH of the cervix.

6. The anti-B-HCG containing microparticles of claim 4, said microparticles having a configuration comprising alternate layers of anti-B-HCG containing layers and anti-B-HCG free matrix material.

7. The anti-B-HCG containing microparticles of claim 1, said microparticles containing from 10 weight % to 60 weight % of anti-B-HCG.

8. The anti-B-HCG containing microparticles of claim 1, said microparticles containing from 10 weight % to 50 weight % of anti-B-HCG.

9. The anti-B-HCG containing microparticles of claim 1, said microparticles containing from 10 weight % to 25 weight % of anti-B-HCG.

10. The anti-B-HCG containing microparticles of claim 4, said microparticles containing from 10 weight % to 60 weight % of anti-B-HCG.

11. The anti-B-HCG containing microparticles of claim 4, said microparticles containing from 10 weight % to 50 weight % of anti-B-HCG.

12. The anti-B-HCG containing microparticles of claim 4, said microparticles containing from 10 weight % to 25 weight % of anti-B-HCG.

13. Anti-B-HCG containing microparticles for the immunization of the internal female reproductive organs, which comprise microparticles having a size of from 10 to 100 μm and containing a biologically effective amount of anti-B-HCG incorporated in a matrix material which is biocompatible and biologically degradable, said microparticles being capable of being transported after deposition in the vagina by the natural transport mechanism of the internal female reproductive organs across the cervix into the uterus wherein immunization is effected within said internal female reproductive organs.

14. The microparticles of claim 13, wherein said microparticles further contain a menstrual cycle regulatory hormone which stimulates said natural transport mechanism.

15. The microcapsules of claim 14, wherein said hormone is estradiol or progesterone.

16. The microparticles of claim 13, wherein said microparticles are of a size ranging from 20 to 70 μm.

17. The microparticles of claim 13, wherein said matrix material is polylactic acid, polyglycolic acid, or copolymers of glycolic and lactic acids.

18. The microparticles of claim 13, wherein said microparticles are of a monolithic structure in which said antibody is dispersed throughout the matrix material.

19. The microparticles of claim 13, wherein said microparticles contain from 10 wt.% to 60 wt.% of said antibody.

* * * * *

UNITED STATES PATENT AND TRADEMARK OFFICE
CERTIFICATE OF CORRECTION

PATENT NO.  : 4,732,763

DATED       : March 22, 1988

INVENTOR(S) : Lee R. Beck

It is certified that error appears in the above-identified patent and that said Letters Patent is hereby corrected as shown below:

Column 1, line 28, delete "regulatd" and insert --regulate--  line 40, delete "femal" and insert --female--.

Column 2, line 11, delete "attempt" and insert --attempted--; line 32, delete "the (second appearing the) and insert --a--; line 51, insert --the-- after "into"; lines 57 and 60, delete "non-motile" and insert --nonmotile--.

Column 3, line 29, delete "natrual" and insert --natural--.

Column 4, line 14, delete "combine" and insert --combines--; line 15, delete "neutralize" and insert --neutralizes--; line 16, delete "precipitate" and insert --precipitates--; line 21, delete "repsonse" and insert --response--; line 26, delete "infections" and insert --infectious--; line 43, delete "endogeneous" and insert --endogenous--; line 54, delete "respsonding" and insert --responding--; line 59, delete "non-toxic" and insert --nontoxic--.

UNITED STATES PATENT AND TRADEMARK OFFICE
CERTIFICATE OF CORRECTION

PATENT NO. : 4,732,763

DATED : March 22, 1988

INVENTOR(S) : Lee R. Beck

It is certified that error appears in the above-identified patent and that said Letters Patent is hereby corrected as shown below:

Column 5, line 1, delete "non-toxic" and insert --nontoxic--; line 15, delete "fallopian" and insert --Fallopian--; line 18, delete "reproduction" and insert --reproductive,--; line 24, delete "endogeneous" and insert --endogenous--.

Column 6, line 9, delete "fallopian" and insert --Fallopian--; line 25, delete "pregestin" and insert --progestin--; line 40, delete "on" and insert --in--; line 52, delete "contratile" and insert --contractile--.

Column 7, line 8, delete "micrparticles" and insert --microparticles--; line 25, delete "administerd" and insert --administered--; line 66, delete "fallopian" and insert --Fallopian--.

Column 8, line 23, delete "urterus" and insert --uterus--.

Column 10, line 34, delete "fallopian" and insert --Fallopian--; line 59, delete "cervis" and insert --cervix--; line 62, delete "fallopian" and insert --Fallopian--.

UNITED STATES PATENT AND TRADEMARK OFFICE
CERTIFICATE OF CORRECTION

PATENT NO. : 4,732,763
DATED : March 22, 1988
INVENTOR(S) : Lee R. Beck

It is certified that error appears in the above-indentified patent and that said Letters Patent is hereby corrected as shown below:

Column 11, line 21, delete "Microplasma" and insert --Mycoplasma--; line 22, delete "Hemophilus" and insert --Haemophilus--; line 25, delete "fetus" in both instances and insert --foetus--; line 32, delete "Actinobaccilus" and insert --Actinobacillus--; lines 58 and 68, delete "fallopian" and insert --Fallopian--.

Column 12, line 19, delete "mumoglobulin" and insert --munoglobulin--; lines 20 and 40, delete "fallopian" and insert --Fallopian--.

Column 13, line 39, delete "method" and insert --methods--.

Column 14, line 2, delete "most" and insert --must--; lines 10 and 19, delete "conservation" and insert --coacervation--; line 32, delete "carful" and insert --careful--; line 68, delete "ae" and insert --are--.

UNITED STATES PATENT AND TRADEMARK OFFICE
CERTIFICATE OF CORRECTION

PATENT NO. : 4,732,763
DATED : March 22, 1988
INVENTOR(S) : Lee R. Beck

It is certified that error appears in the above-indentified patent and that said Letters Patent is hereby corrected as shown below:

Column 15, line 24, delete "microencapulsation" and insert --microencapsulation--; line 49, delete "in" and insert --to--.

Column 16, line 14, delete "suppository Four," and insert --suppository. Four, --; line 53, delete "fallopian" and insert --Fallopian--; line 58, delete "veneral" and insert --venereal--; line 61, delete "fallopian" and insert --Fallopian--.

Column 17, line 4, delete "syphillis" and insert --syphilus--; line 15, delete "occuring" and insert --occurring--; lines 28, 38 and 68, delete "fallopian" and insert --Fallopian--.

Column 18, line 5, delete "fallopian" and insert --Fallopian--.

UNITED STATES PATENT AND TRADEMARK OFFICE
CERTIFICATE OF CORRECTION

PATENT NO. : 4,732,763
DATED : March 22, 1988
INVENTOR(S) : Lee R. Beck

It is certified that error appears in the above-indentified patent and that said Letters Patent is hereby corrected as shown below:

Column 19, line 55, delete "teflon" and insert --Teflon--; line 61, delete "hCG" and insert --HCG--; line 65, delete "micro droplets" and insert --microdroplets--.

Column 20, line 8, delete "micro droplets" and insert --microdroplets--; line 51, delete "sub unit" and insert --subunit--; line 51, delete "hCG" and insert --HCG--; line 55, delete "existance" and insert --existence--; line 57, delete "subunit" and insert --subunit--; line 57, delete "hCG" and insert --HCG--.

UNITED STATES PATENT AND TRADEMARK OFFICE
CERTIFICATE OF CORRECTION

PATENT NO. : 4,732,763
DATED : March 22, 1988
INVENTOR(S) : Lee R. Beck

It is certified that error appears in the above-indentified patent and that said Letters Patent is hereby corrected as shown below:

Column 21, Table I, line 5, delete "hCG" and insert --HCG--.

line 30, delete "he" and insert --The--;

line 33, delete "hCG" and insert --HCG--;

line 40, delete "hCG" and insert --HCG--;

lines 32 and 45, delete "sub unit" and insert --subunit--;

line 51, delete "bovine" and insert --Bovine--;

line 53, delete "hCG" and insert --HCG--;

line 54, delete "bovine" and insert --Bovine--;

line 55, delete "her-" and insert --Her- --;

line 59, delete "hCG" and insert --HCG--;

lines 63 and 64, delete "bovine" and insert --Bovine--.

UNITED STATES PATENT AND TRADEMARK OFFICE
CERTIFICATE OF CORRECTION

PATENT NO. : 4,732,763
DATED : March 22, 1988
INVENTOR(S) : Lee R. Beck

It is certified that error appears in the above-indentified patent and that said Letters Patent is hereby corrected as shown below:

Column 22, line 37, delete "microcapsules" and insert --microparticles--.

Column 22, Table I, line 5, delete "hCG" and insert --HCG--.

Column 24, Claim 15, delete "microcapsules" and insert --microparticles--.

Signed and Sealed this

Seventeenth Day of May, 1994

Attest:

BRUCE LEHMAN

Attesting Officer

Commissioner of Patents and Trademarks